US00PP29588P3

(12) United States Plant Patent
Ichie

(10) Patent No.: US PP29,588 P3
(45) Date of Patent: Aug. 14, 2018

(54) ***HYDRANGEA* PLANT NAMED 'TOMEINA-BLUE'**

(50) Latin Name: *Hydrangea macrophylla*
Varietal Denomination: Tomeina-blue

(71) Applicant: Toyokazu Ichie, Kakegawa (JP)

(72) Inventor: Toyokazu Ichie, Kakegawa (JP)

( * ) Notice: Subject to any disclaimer, the term of this patent is extended or adjusted under 35 U.S.C. 154(b) by 1 day.

(21) Appl. No.: 15/530,966

(22) Filed: Mar. 29, 2017

(65) Prior Publication Data

US 2017/0347514 P1 Nov. 30, 2017

Related U.S. Application Data

(60) Provisional application No. 62/392,267, filed on May 25, 2016.

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Anne Marie Grunberg
(74) *Attorney, Agent, or Firm* — Audrey Charles

(57) ABSTRACT

A new and distinct cultivar of *Hydrangea* plant named 'Tomeina-blue', characterized by its light purple-colored inflorescences that are pale blue-colored when grown under acidic soil conditions, dark green-colored foliage, and moderately vigorous, upright growth habit, is disclosed.

1 Drawing Sheet

Latin name of genus and species of plant claimed: *Hydrangea macrophylla.*

Variety denomination: 'Tomeina-blue'.

BACKGROUND OF THE INVENTION

The present invention relates to a new and distinct cultivar of *Hydrangea* plant botanically known as *Hydrangea macrophylla* and hereinafter referred to by the cultivar name 'Tomeina-blue'.

The new cultivar originated in a controlled breeding program in Kakegawa, Japan during June 2008. The objective of the breeding program was the development of *Hydrangea* cultivars that have double-type, blue-colored inflorescences when grown under acidic soil conditions.

The new *Hydrangea* cultivar is the result of cross-pollination. The female (seed) parent of the new cultivar is 'Morino-izumi', not patented, characterized by its single-type, pink-colored inflorescences that are light blue-colored when grown under acidic soil conditions, dark green-colored foliage, and vigorous, upright growth habit. The male (pollen) parent of the new cultivar is a proprietary *Hydrangea macrophylla* breeding selection coded 03-10A, not patented, characterized by is double-type, pink-colored inflorescences having white-colored margins that are purple-colored with white-colored margins when grown under acidic soil conditions, dark green-colored foliage, and moderately vigorous, upright growth habit. The new cultivar was discovered and selected as a single flowering plant within the progeny of the above stated cross-pollination during July 2010 in a controlled environment in Kakegawa, Japan.

Asexual reproduction of the new cultivar by terminal stem cuttings since July 2010 in Kakegawa, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Tomeina-blue' as a new and distinct cultivar of *Hydrangea* plant:

1. Double-type, light purple-colored inflorescences that are pale blue-colored when grown under acidic soil conditions;
2. Dark green-colored foliage; and
3. Moderately vigorous, upright growth habit.

Plants of the new cultivar differ from plants of the female parent primarily in flower type and in having reduced growth vigor. Plants of the new cultivar differ from plants of the male parent primarily in inflorescence color.

Of the many commercially available *Hydrangea* cultivars, the most similar in comparison to the new cultivar is 'Inspire', U.S. Plant Pat. No. 26,824. However, in comparison, plants of the new cultivar differ from plants of 'Inspire' in at least the following characteristics:

1. Plants of the new cultivar have more sepals per sterile floret than plants of 'Inspire';
2. Plants of the new cultivar have a first open sterile floret color that is different from plants of 'Inspire'; and
3. Plants of the new cultivar have a more compact habit than plants of 'Inspire'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tomeina-blue'. The plants were approximately 10 months old and grown in 2-gallon containers in an outdoor nursery in West Grove, Pa.

for approximately 6 months then transferred to greenhouse conditions for approximately 4 months in West Grove, Pa.

DETAILED BOTANICAL DESCRIPTION

Figure 1:
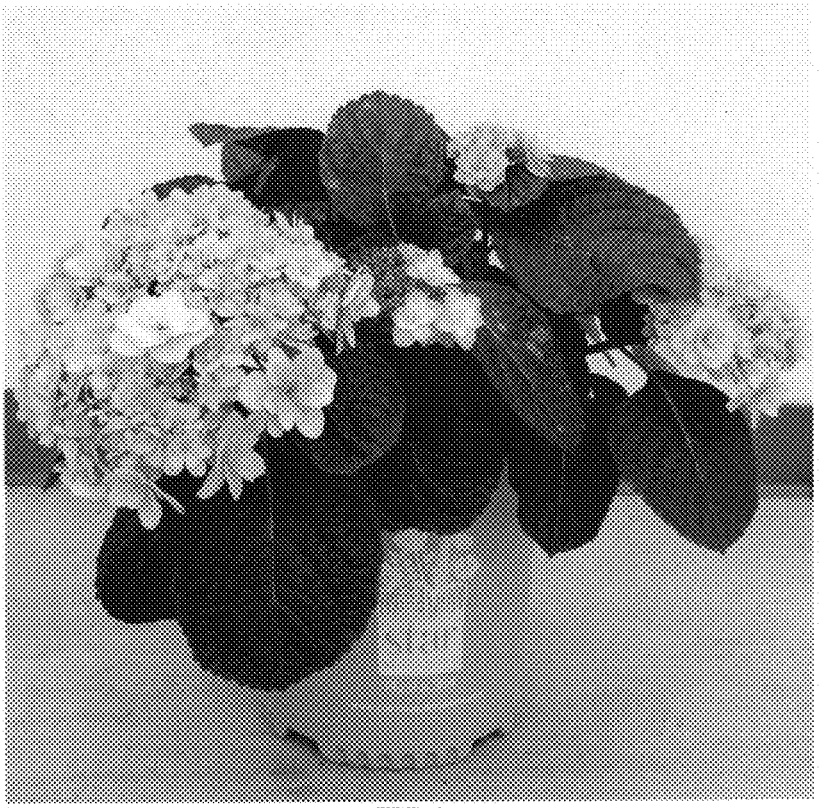
FIG. 1 illustrates a side view of the overall growth and flowering habit of 'Tomeina-blue'.
Figure 2:
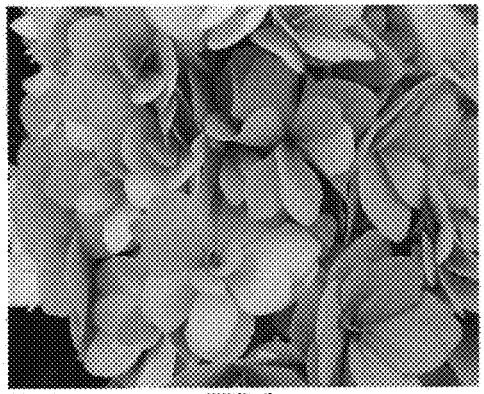
FIG. 2 illustrates a close-up view of an inflorescence of 'Tomeina-blue'
Figure 3:
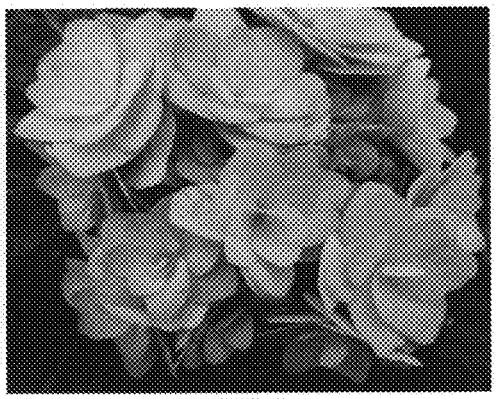
FIG. 3 illustrates a close-up view of an inflorescence of 'Tomeina-blue' when grown under acidic soil conditions.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2017 under natural light conditions in West Grove, Pa.

The following descriptions and measurements describe approximately 10 month old plants produced from cuttings from stock plants. Plants grown under acidic conditions were treated with aluminum sulfate at a rate of 0.16 oz per 1 gallon every seven days for a total of three treatments. The plants were grown in 2-gallon containers utilizing a soilless growth medium for approximately 6 months in an outdoor nursery in West Grove, Pa. then moved indoors and held under greenhouse conditions for approximately 4 months to flower. Greenhouse temperatures were maintained at 74° F. to 80° F. (23° C. to 27° C.) during the day and approximately 66° F. to 70° F. (19° C. to 21° C.) during the night. Greenhouse light levels of 2,100 footcandles to 4,122 footcandles were maintained during the day. Measurements and numerical values represent averages of typical plants.

Botanical classification: *Hydrangea macrophylla* cultivar Tomeina-blue.

Parentage:

*Female parent.*—'Morino-izumi', not patented.

*Male parent.*—Proprietary *Hydrangea macrophylla* breeding selection coded 03-10A, not patented.

Propagation:

*Type cutting.*—Softwood cuttings.

*Time to initiate roots.*—Approximately 20 to 25 days.

*Time to produce a rooted cutting.*—Approximately 30 to 35 days.

*Root description.*—Medium thickness, fleshy, white, NN155D.

*Rooting habit.*—Moderate branching, moderately dense.

Plant description:

*Commercial crop time.*—Approximately 12 months from a rooted cutting to finish in a 3-gallon container.

*Growth habit and general appearance.*—Deciduous shrub, mophead-type *Hydrangea*; moderately vigorous, upright growth habit.

*Hardiness.*—USDA Zone 5 (−20° F. to −15° F.).

*Heat tolerance.*—Regularly tolerates temperatures as high as 33.9° C. in the summer.

*Size.*—Height from soil level to top of plant plane: Approximately 29.0 cm. Width: Approximately 50.0 cm.

*Branching habit.*—Freely branching. Quantity of lateral branches per plant: Approximately 9.

*Branch.*—Shape: Rounded. Strength: Strong. Length to base of inflorescence: Approximately 17.0 cm. Diameter: Approximately 5.0 mm. Length of central internode: Approximately 6.0 cm. Texture of young stem: Glabrous. Texture of mature stem: Woody. Color of young stem: 146C. Color of mature stem: 144A.

*Lenticels.*—Quantity per internode: Approximately 47. Shape: Round to elliptic. Size: Approximately 0.5 mm to 1.0 mm. Color: 165A.

Foliage description:

*General description.*—Quantity of leaves per lateral branch: Approximately 6. Fragrance: None detected. Form: Simple. Arrangement: Opposite.

*Leaves.*—Aspect: Flat. Shape: Elliptic. Margin: Serrated. Apex: Acuminate. Base: Rounded. Venation pattern: Pinnate. Length of mature leaf: Approximately 12.5 cm. Width of mature leaf: Approximately 7.0 cm. Texture of upper and lower surfaces: Coriaceous, glabrous. Color of upper surface of young foliage: 146A with venation of 143C. Color of lower surface of young foliage: 146B with venation of 146D. Color of upper surface of mature foliage: 147A with 139A and venation of 147B. Color of lower surface of mature foliage: 147B and 138A with venation of 147C.

*Petiole.*—Length: Approximately 1.0 cm. Diameter: Approximately 4.0 mm. Texture: Glabrous. Color: 144C.

Flowering description:

*Flowering habit.*—Seasonal, May through August.

*Lastingness of individual inflorescence on the plant.*—Persistent, color retained for about 3 to 4 weeks.

Inflorescence description:

*General description.*—Type: Terminal globular, mophead, compound corymb of double-type, sterile flowers composed of an average of 18 sepals, fertile flowers form buds that do not open. Quantity per plant: One per lateral or sublateral stem. Fragrance: None detected. Aspect: Face upward and outward. Height: Approximately 8.0 cm. Width: Approximately 21.0 cm. Quantity of fertile florets per inflorescence: Approximately 100. Quantity of sterile florets per inflorescence: Approximately 130.

*Peduncle.*—Strength: Strong. Shape: Rounded. Length: Approximately 3.0 cm. Diameter: Approximately 5.0 mm. Texture: Glabrous. Color: 144A.

Floret description:

*General description.*—Type: Double, sterile; fertile flowers form buds that do not open.

*Sterile florets, bud just before opening.*—Shape: Globular. Length: Approximately 5.0 mm. Diameter: Approximately 5.0 mm. Color: 143C.

*Sterile florets.*—Depth: Approximately 1.5 cm. Diameter: Approximately 3.5 cm.

*Sepals, sterile florets.*—Shape: Obovate. Margin: Entire. Apex: Broadly acute. Base: Broadly attenuate. Length: Approximately 6.0 mm to 1.8 cm. Width: Approximately 3.0 mm to 1.3 cm. Texture of upper and lower surfaces: Glabrous. Color of upper surface when first open: NN155D with 73B at apex, under acidic soil conditions 155A mottled with 76C. Color of lower surface when first open: NN155D with between 73B and 73C at apex, under acidic soil conditions NN155D with between 76C and 76D at apex. Color of upper and lower surfaces when fully open: Closest to 75B, with senescence fades to lighter than 75D often nearing NN155A and tinted with 144A; under acidic soil conditions closest to 115D, with senescence fades to lighter than 115D often nearing NN155A and tinted with 144A.

*Pedicel, sterile florets.*—Strength: Strong. Aspect: Erect to approximately 90° from peduncle axis. Length: Approximately 1.5 cm. Diameter: Approximately 3.0 mm. Texture: Sparsely pubescent with appressed hairs. Color: 144A.

*Fertile florets, bud.*—Shape: Globular. Length: Approximately 1.0 mm. Diameter: Approximately 1.0 mm. Color: 143C.

*Reproductive organs.*—Not observed.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'Tomeina-blue', substantially as herein illustrated and described.

* * * * *